United States Patent
Humphreys

(10) Patent No.: US 10,426,483 B2
(45) Date of Patent: Oct. 1, 2019

(54) HEMOSTATIC DEVICES AND METHODS FOR USE THEREOF

(71) Applicant: Mitchell R. Humphreys, Cave Creek, AZ (US)

(72) Inventor: Mitchell R. Humphreys, Cave Creek, AZ (US)

( * ) Notice: Subject to any disclaimer, the term of this patent is extended or adjusted under 35 U.S.C. 154(b) by 44 days.

(21) Appl. No.: 15/402,869

(22) Filed: Jan. 10, 2017

(65) Prior Publication Data

US 2017/0209148 A1 Jul. 27, 2017

Related U.S. Application Data

(63) Continuation-in-part of application No. 13/712,486, filed on Dec. 12, 2012, now Pat. No. 9,539,381, (Continued)

(51) Int. Cl.
| | |
|---|---|
| *A61B 17/12* | (2006.01) |
| *A61M 25/00* | (2006.01) |
| *A61B 17/34* | (2006.01) |
| *A61L 29/16* | (2006.01) |
| *A61M 5/00* | (2006.01) |
| *A61M 39/06* | (2006.01) |
| *A61B 17/00* | (2006.01) |
| *A61B 17/22* | (2006.01) |
| *A61B 90/40* | (2016.01) |

(52) U.S. Cl.
CPC .......... *A61B 17/12* (2013.01); *A61B 17/3421* (2013.01); *A61L 29/16* (2013.01); *A61M 5/00* (2013.01); *A61M 25/0045* (2013.01); *A61M 39/06* (2013.01); *A61B 17/0057* (2013.01); *A61B 90/40* (2016.02); *A61B 2017/12004* (2013.01); *A61B 2017/22038* (2013.01); *A61B 2017/3443* (2013.01); *A61B 2017/3486* (2013.01); *A61B 2017/3488* (2013.01); *A61L 2400/04* (2013.01); *A61L 2430/26* (2013.01); *A61M 2039/0633* (2013.01)

(58) Field of Classification Search
CPC .............. A61B 17/12; A61B 17/12022; A61B 17/3421; A61B 2017/3488; A61B 2017/12004; A61B 17/0057; A61B 17/8805; A61B 90/40; A61B 2017/22038; A61B 2017/3443; A61B 2017/3486; A61M 39/06; A61M 5/00; A61M 25/0045; A61M 2039/0633; A61L 29/16; A61L 2400/04; A61L 2430/26
See application file for complete search history.

(56) References Cited

U.S. PATENT DOCUMENTS

| | | |
|---|---|---|
| 2,078,686 A | 4/1937 | Rowe |
| 4,781,690 A | 11/1988 | Ishida et al. |

(Continued)

OTHER PUBLICATIONS

Leung, Lawrence L.K., M.D., Overview of Hemostatis, pp. 1-18, © 2013 UpToDate, Inc.

(Continued)

*Primary Examiner* — Darwin P Erezo
*Assistant Examiner* — Erich Herbermann
(74) *Attorney, Agent, or Firm* — Banner & Witcoff, Ltd.

(57) ABSTRACT

Materials and methods for reducing or preventing bleeding and associated side effects during and after percutaneous medical procedures.

3 Claims, 18 Drawing Sheets

Related U.S. Application Data which is a continuation-in-part of application No. 12/464,583, filed on May 12, 2009, now Pat. No. 8,709,039.

(60) Provisional application No. 61/052,537, filed on May 12, 2008.

(56) References Cited

U.S. PATENT DOCUMENTS

| | | |
|---|---|---|
| 4,994,033 A | 2/1991 | Shockey et al. |
| 5,320,639 A | 6/1994 | Rudnick |
| 5,324,261 A | 6/1994 | Amundson et al. |
| 5,413,571 A * | 5/1995 | Katsaros ............ A61B 17/0057 128/899 |
| 5,433,691 A * | 7/1995 | Hiraoka ................ B65H 27/00 492/45 |
| 5,437,631 A | 8/1995 | Janzen |
| 5,514,158 A | 5/1996 | Kanesaka |
| 5,545,132 A | 8/1996 | Fagan et al. |
| 5,634,901 A | 6/1997 | Alba et al. |
| 5,725,551 A * | 3/1998 | Myers ................ A61B 17/0057 604/285 |
| 7,758,892 B1 | 7/2010 | Chen et al. |
| 7,846,171 B2 | 12/2010 | Kullas et al. |
| 8,114,049 B2 | 2/2012 | Freyman et al. |
| 8,201,563 B2 | 6/2012 | Conquergood et al. |
| 8,709,039 B2 | 4/2014 | Humphreys |

OTHER PUBLICATIONS

Nov. 25, 2015—(US) Office Action—U.S. Appl. No. 14/200,457.
Mar. 16, 2016—(US) Non-Final Office Action—U.S. Appl. No. 14/325,805.
Mar. 2, 2016—(US) Final Office Action—U.S. Appl. No. 13/712,486.
Jun. 8, 2016—(US) Final Office Action—U.S. Appl. No. 14/200,457.
Oct. 6, 2016—(US) Office Action—U.S. Appl. No. 13/712,486.

* cited by examiner

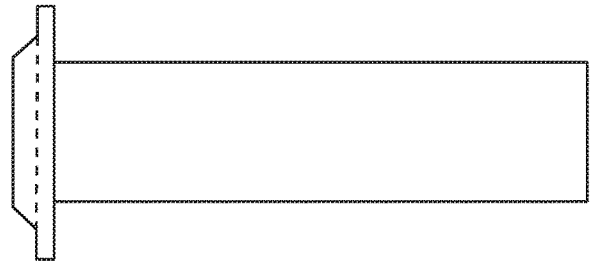
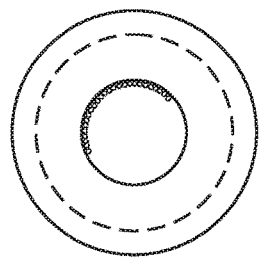
FIG. 8A                FIG. 8B
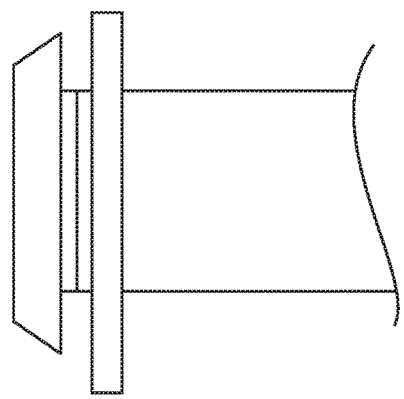
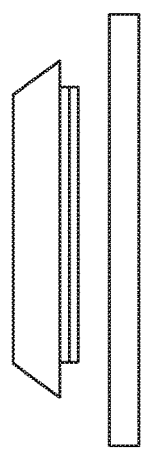
FIG. 8C                FIG. 8D

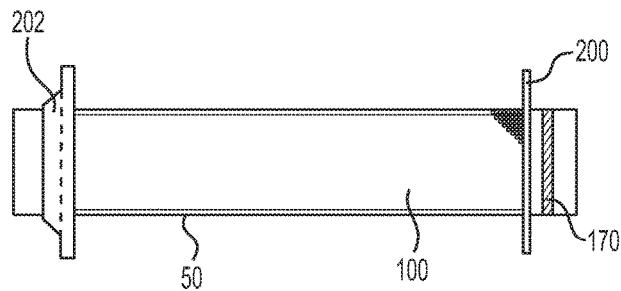 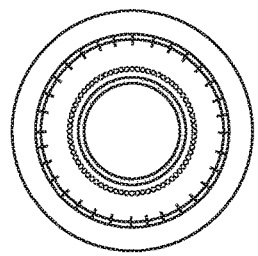
*FIG. 8E*        *FIG. 8F*
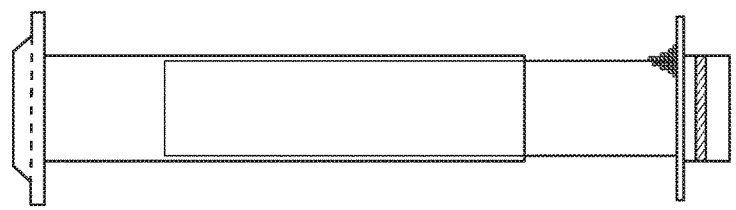
*FIG. 8G*
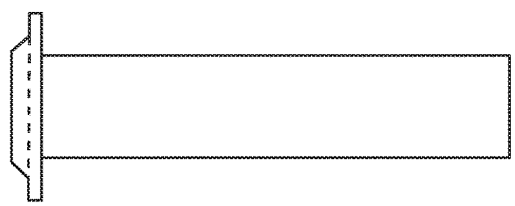 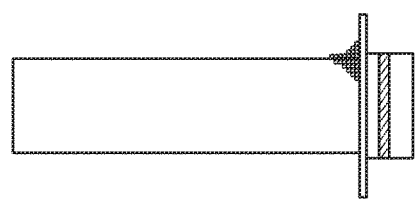
*FIG. 8H*        *FIG. 8I*

FIG. 9A  FIG. 9B

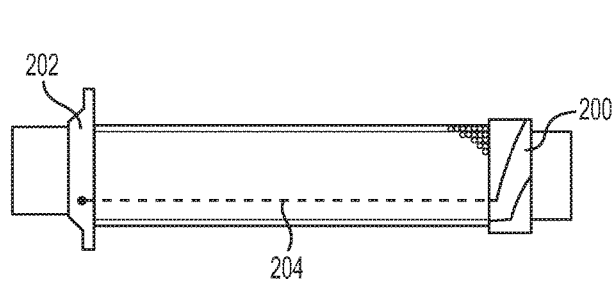 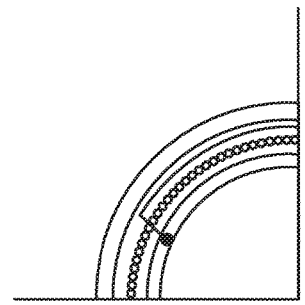
*FIG. 10A*  *FIG. 10B*
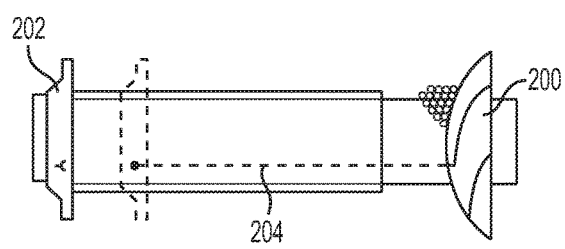 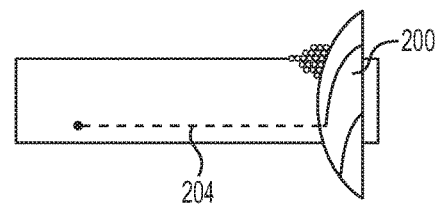
*FIG. 10C*  *FIG. 10D*
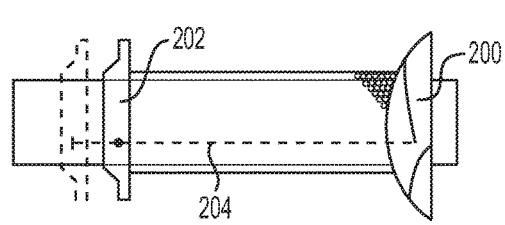 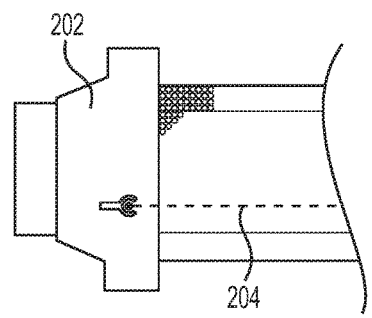
*FIG. 10E*  *FIG. 10F*

HEMOSTATIC DEVICES AND METHODS FOR USE THEREOF

CROSS-REFERENCE TO RELATED APPLICATIONS

This application is a Continuation-in Part of co-pending U.S. application Ser. No. 13/712,486 (filed Dec. 12, 2012), which is a Continuation-In-Part application of co-pending U.S. application Ser. No. 12/464,583 (filed May 12, 2009), which claims priority to Provisional Patent Application No. 61/052,537 (filed May 12, 2008), which applications are entirely incorporated herein by reference and made a part hereof.

TECHNICAL FIELD

This document relates to devices and methods for hemostasis during percutaneous medical procedures.

BACKGROUND

Percutaneous renal procedures can be used for a variety of medical purposes, including removal of kidney stones that are too large or too complex to be removed by another method, to remove or treat urothelial cancer in the urinary collecting system, or to treat kidney obstruction. These percutaneous surgical techniques generally utilize radiographic imagining to determine the precise location for desired access to a kidney. Using a needle, a puncture is made through the back and underlying tissues into the kidney. Once the tract has been established, a "safety" wire typically is passed from outside the body, through the kidney, and down the ureter toward the bladder. The tract is then dilated with a balloon or a rigid dilator, and a percutaneous sheath is placed over the dilating device. The sheath provides a portal through which different instruments and scopes can be placed in order to complete the percutaneous renal procedure.

SUMMARY

As many as a third of patients who undergo a percutaneous renal procedure will require a blood transfusion due to bleeding from the puncture of the kidney. Such bleeding can cause severe complications, including loss of renal function, pain, prolonged hospitalization, need for selective arterial embolization, or even the need for surgical removal of the kidney. This document provides hemostatic devices and methods for their use, which can reduce or prevent bleeding in percutaneous renal procedures and thus can reduce the risk of subsequent side effects. The devices provided herein can be readily deployed with minimal risk to the patient, and can be used for any suitable percutaneous procedure, including treatment of kidney stones, kidney biopsy, management of upper urinary tract cancers, or drainage of the kidney through a subject's back.

In one aspect, this document features an article comprising an elongate member having an exterior surface, a hemostatic material in contact with at least a portion of the exterior surface, and a covering that surrounds the hemostatic material and is adapted to move slidably over the elongate member. The elongate member can comprise a first end and a second end. The hemostatic material can be in contact with a portion of the external surface adjacent to the first end, and can extend over the hemostatic material from the first end toward the second end. The covering can extend to the second end, and can comprise a protrusion adjacent to the second end. The elongate member can have an interior lumen extending from the first end to the second end. The article can have a diameter of 20 to 26 French and a length from about 3 cm to about 20 cm. The elongate member can comprise a first portion having a first diameter and a second portion having a second diameter. The first diameter can be less than the second diameter, and the hemostatic material can be coated on the first portion.

In another aspect, this document features a kit comprising an article and a driver as described herein.

In another aspect, this document features a method for reducing bleeding in a subject during or after a medical procedure that includes utilizing a percutaneous sheath to gain access to an internal organ, the method comprising inserting an article as described herein into the subject through the percutaneous sheath, and actuating the article such that the tissue of the subject is contacted by the hemostatic material. The internal organ can be a kidney.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 8A is a side view of an exemplary embodiment of a hemostatic device.

FIG. 8B is a cross-sectional view of the device shown in FIG. 8A.

FIGS. 8C-8D are side view of an exemplary embodiment of a hemostatic device.

FIG. 8E is a side view of an exemplary embodiment of a hemostatic device.

FIG. 8F is a cross-sectional view of the hemostatic device shown in FIG. 8E.

FIGS. 8G-8I are side views of exemplary embodiments of a hemostatic device.

FIG. 9A is a side view of an exemplary embodiment of a hemostatic device.

FIG. 9B is a cross-sectional view of the hemostatic device shown in FIG. 9A.

FIG. 10A is a side view of an exemplary embodiment of a hemostatic device.

FIG. 10B is a partial cross-sectional view of the hemostatic device shown in FIG. 10A.

FIGS. 10C-10I are side views of exemplary embodiments of a hemostatic device.

Like reference symbols in the various drawings indicate like elements.

DETAILED DESCRIPTION

Figure 1:
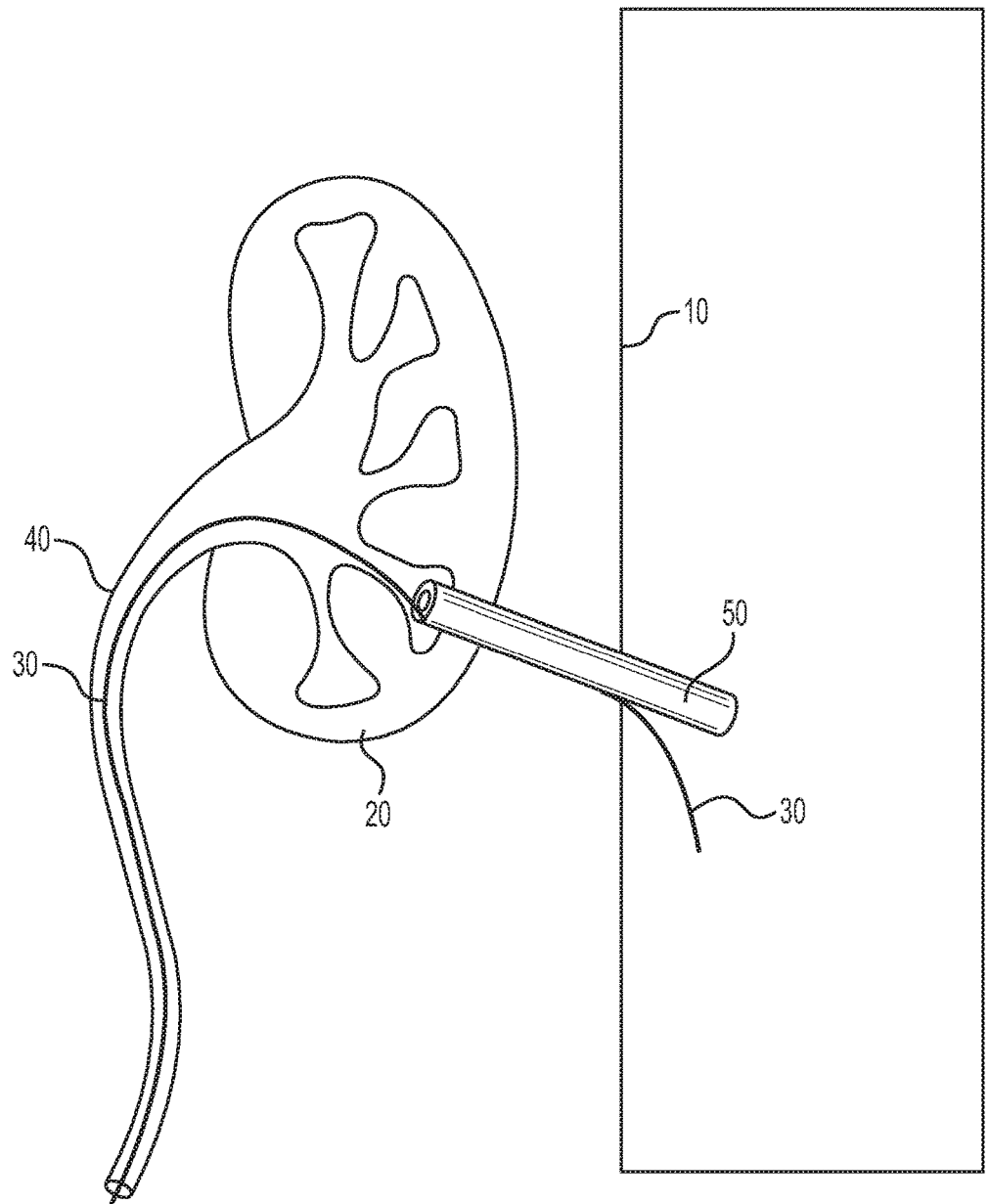
FIG. 1 is a depiction of a typical percutaneous renal procedure.

This document provides hemostatic devices and methods for their use in percutaneous procedures (e.g., percutaneous renal procedures). A typical percutaneous renal procedure is depicted in FIG. 1. A puncture is made through skin 10 of a subject's back, through the underlying tissues, and into kidney 20. Once a tract has been established, one or more wires (e.g., wire 30) can be passed through the tract, through the kidney, and down ureter 40 toward the bladder. When two wires are present, for example, a dilating device can be placed over one of the wires (the "working wire"), while the other wire (the "safety wire") can be along the outside of the dilating device. The tract then can be dilated, and percutaneous sheath 50 can be placed over the dilating device. Either the working wire or the safety wire can serve as a guide in case sheath 50 becomes displaced during a subsequent procedure. The size of sheath 50 can vary depending on the specific procedure, but often is 30 French (10.0 mm) in diameter. Sheath 50 can be hollow, providing a portal through which different instruments and scopes can be placed into the patient. Upon completion of a procedure, sheath 50 can be withdrawn from the subject, whereupon bleeding may occur from the kidney as well as the soft tissue and muscle of the back along the insertion/removal tract. The hemostatic devices described herein can be used to reduce or prevent such bleeding, as well as the associated side effects.

FIGS. 2A-G and 3 provide depictions of exemplary hemostatic devices according to some embodiments provided herein. Device 100 can comprise cylinder 105 having proximal portion 110, proximal end 115, distal portion 120, distal end 125, and exterior surface 130. In some embodiments, cylinder 105 can be hollow such that it has an interior lumen extending through its length. This can allow for passage of, for example, wires, nephrostomy tubes, scopes, or any other suitable articles through device 100.

Device 100 can have any suitable size, and can be configured to move slidably within a percutaneous sheath. The most commonly used percutaneous sheaths have diameters of 24, 28, and 30 French (8.0, 9.3, and 10.0 mm, respectively). The devices provided herein can be 4 to 8 French less in diameter than the percutaneous sheath (e.g., 16, 18, 20, 22, 24, or 26 French). Further, device 100 can have any suitable length. For example, cylinder 105 can have a length from about 8 cm to about 22 cm (e.g., about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm; or about 22 cm). In addition, the devices can be made from any suitable material, including, for example, plastic.

Device 100 can have hemostatic material 140 coated on all or a portion of exterior surface 130 of cylinder 105. Hemostatic material 140 can accelerate a subject's natural ability to form blood clots. Any suitable hemostatic material can be used, including, without limitation, anti-fibrinolytics, fibrin sealants, matrix hemostats, and topical hemostatic agents. Particular examples of hemostatic materials include, without limitation, gelatins such as SURG1FOAM™ (Johnson & Johnson; Piscataway, N.J.) and GELFOAM® (Pharmacia & Upjohn Co.; New York, N.Y.); collagen materials such as AVITENE® and ULTRAFOAM™ (CR. Bard, Inc.; Murray Hill, N.J.); oxidized regenerated cellulose materials such as SURGICEL® Fibrillar and NU-KNIT™ (Johnson & Johnson); thrombin (e.g., pooled human or bovine thrombin); fibrin sealants such as TISSEEL® (Baxter Healthcare Corp.; Westlake Village, Calif.), EVICEL™ (Johnson & Johnson), VITAGEL™ (Orthovita, Inc.; Malvern, Pa.), and HEMASEEL® (Haemacure Corp.; Montreal, Quebec); polyethylene glycol polymers such as COSEAL® (Baxter Healthcare) and DURASEAL® (Confluent Surgical; Waltham, Mass.); albumin and glutaraldehyde compositions such as B1OGLUE® (Cryolife Inc.; Kennesaw, Ga.) and FOCALSEAL® (Focal, Inc.; Lexington, Mass.); glutaraldehyde resorcinol formalin and collagen (GRF; C. R. Bard, Inc.); gelatin and thrombin compositions such as FLOSEAL® (Baxter Healthcare Corp.) and SURGIFLO® (Johnson 8,z Johnson); granular zeolite powders such as QUIKCLOT® (Z-Medica Corp.; Wallingford, Conn.); chitin compositions such as HEMCON® (HemCon Medical Technologies, Inc.; Portland, Oreg.); and microporous polysaccharide hemospheres such as MPH® (Medafor Inc., Minneapolis, Minn.). Hemostatic material 140 can be dissolvable in urine and can be quickly reabsorbed to prevent clots or plugs in the urinary tract, fistulas (abnormal connections between the urinary collecting system and the retroperitoneum or back), or other problems.

Figure 2A:
FIGS. 2A-2G are depictions of exemplary embodiments of a hemostatic device.
Figure 2B:
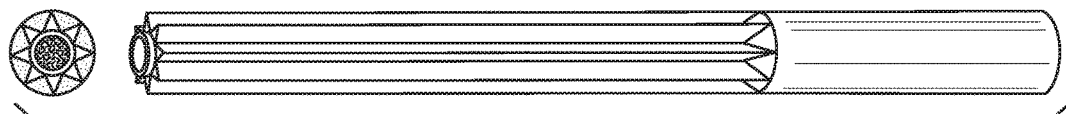
Figure 2C:
Figure 2D:
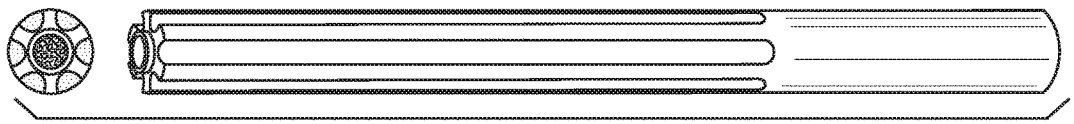
Figure 2E:
Figure 2F:
Figure 2G:
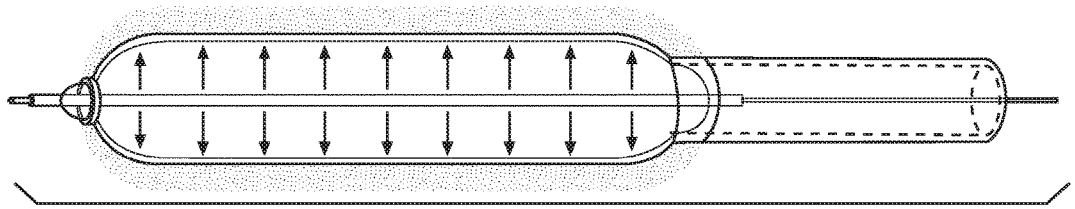

The entirety of exterior surface 130 can be coated with hemostatic material 140, or just a portion (e.g., distal portion 120) can be coated with hemostatic material 140. As shown in FIG. 2, for example, the diameter of cylinder 105 can vary along its length, such that it can have a smaller diameter in some areas than in others. Regions of smaller diameter can serve as reservoirs or channels for a hemostatic material. The diameter of distal portion 120 can be reduced as compared to the diameter of proximal portion 110, and hemostatic material 140 can be placed over distal portion 120. In some cases, for example, outer surface 130 of cylinder 105 can define one or more channels (e.g., channels extending from distal end 125 along distal portion 120 toward proximal end 115 that are perpendicular to the longitudinal axis of cylinder 105, or that are at an angle with respect to the longitudinal axis of cylinder 105, or channels that extend laterally around the circumference of outer surface 130 within distal portion 120). Such embodiments, shown in FIG. 2 for example, have portions of relatively reduced diameter that allow device 100 to hold a greater amount of hemostatic agent 140 where it will be needed most, i.e., near distal end 125, which can be placed in contact with kidney tissue. The cross-sectional shape of the channels or areas of reduced diameter may vary. As shown in FIGS. 2b-2d, for example, the channels or areas of reduced diameter could be V-shaped, rectangular, or semicircular in cross-section, The diameter of cylinder 105 can also provide circumferential pressure along the percutaneous tract while hemostatic material 140 takes effect. The cylinder 105 may also be inflatable, as shown FIG. 2F and FIG. 2G. The hemostatic material may extend around the circumference of the outer surface of the inflatable cylinder 105, as shown in FIG. 2F, thereby placing the hemostatic material in circumferential contact with kidney tissue as the cylinder 105 becomes inflated, as shown in FIG. 2G. The outer surface of the cylinder 105 can provide pressure along the percutaneous tract of the kidney while the hemostatic material takes effect.

Device 100 also can include barrier 150 over hemostatic material 140. Barrier 150 can be, for example, a thin plastic film, and can be broken and/or removed at the time the percutaneous sheath is removed to allow for precise deployment of hemostatic material 140 along the course of the percutaneous tract. In some embodiments, barrier 150 can be a heat sealed plastic covering that can break away at distal end 125. In some cases, barrier 150 can be scored or perforated at or near distal end 125 to facilitate breakage and removal of barrier 150. The presence of barrier 150 over hemostatic material 140 can prevent early activation or dislodgement of material 140, as most percutaneous tubes are subjected to a constant flow of blood, irrigant (normal saline), or urine during use. Further, exterior surface 130 of cylinder 105, which interfaces with hemostatic material 140, can be negatively charged, sufficiently slick, or coated in such a way that hemostatic material 140 will preferably maintain contact with bodily tissue rather than with device 140 once barrier 150 is broken and/or removed. For example, exterior surface 130 can be coated with TEFLON®. This can facilitate removal of device 100 after a suitable length of time (e.g about 30 seconds to about 5 minutes), without dislodging a newly formed clot.

Device 100 also can have a protrusion (e.g., handle or collar 160) that is connected to barrier 150 and that can be actuated to break or remove barrier 150 from device 100 in order to expose hemostatic material 140. Collar 160 can be located at or near proximal end 115 of cylinder 105. By pulling on collar 160 in a proximal direction, a user can break barrier 150 (e.g., at distal end 125) and then pull barrier 150 proximally over the surface of cylinder 105, exposing hemostatic agent 140 to the surrounding tissue.

Figure 3:
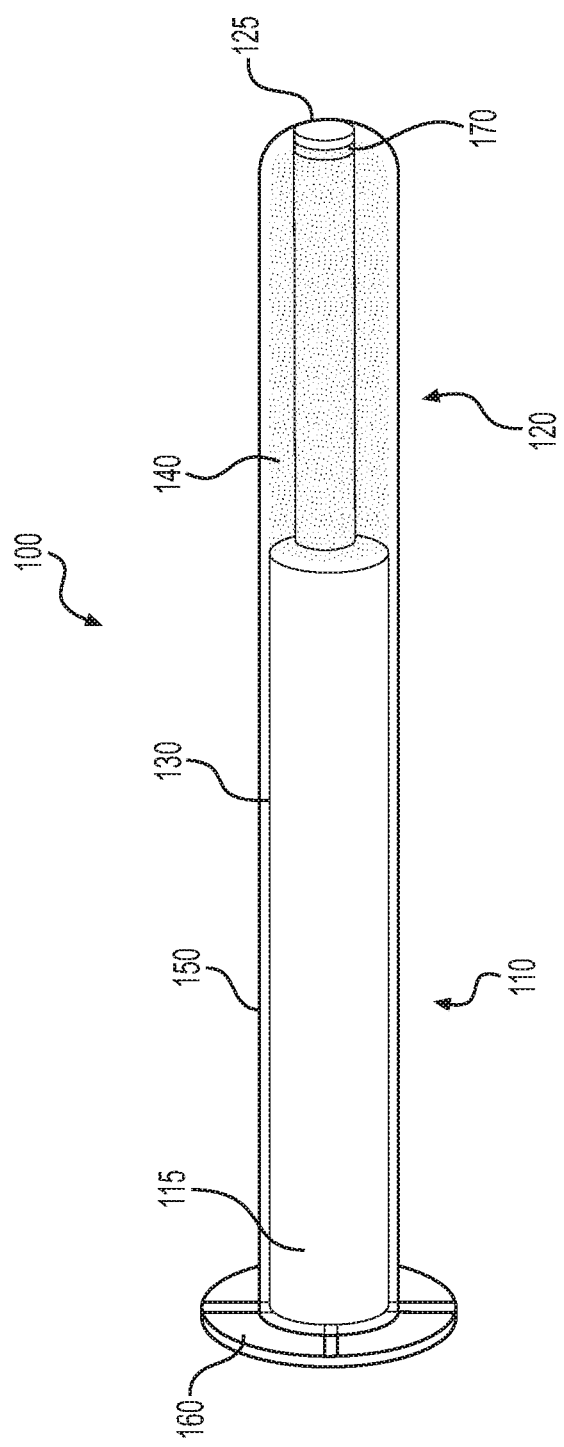
FIG. 3 is a side view of an embodiment of a hemostatic device.

Device 100 also can have include one or more radio-opaque markers (e.g., radio-opaque marker 170) so that the position of device 100 can be observed radiographically during deployment. Cylinder 105 of device 100 also can allow for visual confirmation of deployment at the edge of the renal tissue. Marker 170 can be positioned anywhere on device 100, e.g., at or around distal end 125 of cylinder 105 as shown in FIG. 3, or along the surface of distal portion 120. Suitable radio-opaque materials are known in the art, as are methods for depositing radio-opaque markers on medical devices.

Figure 4:
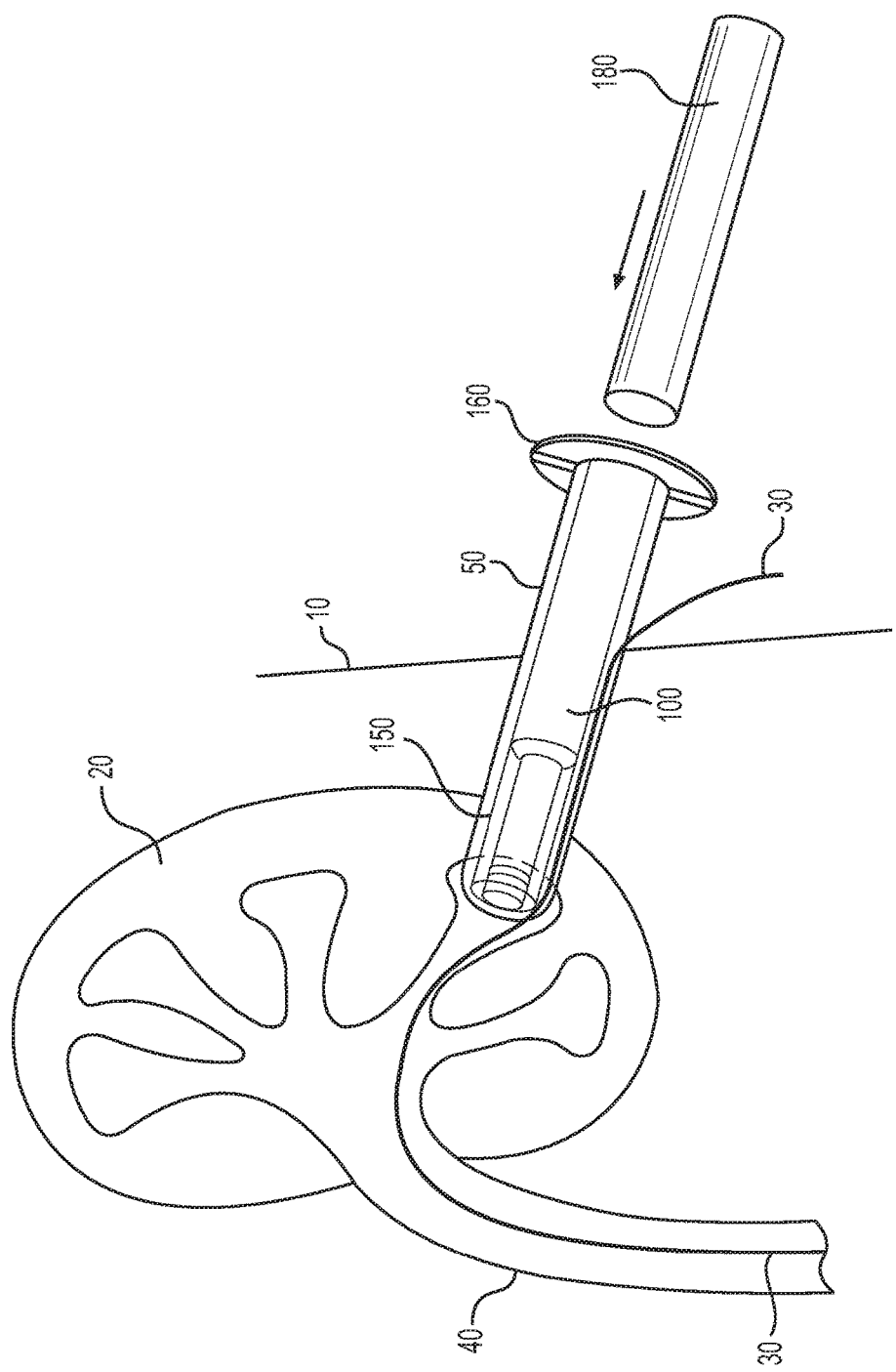
FIG. 4 is a side view of an embodiment of a hemostatic device in use.
Figure 5:
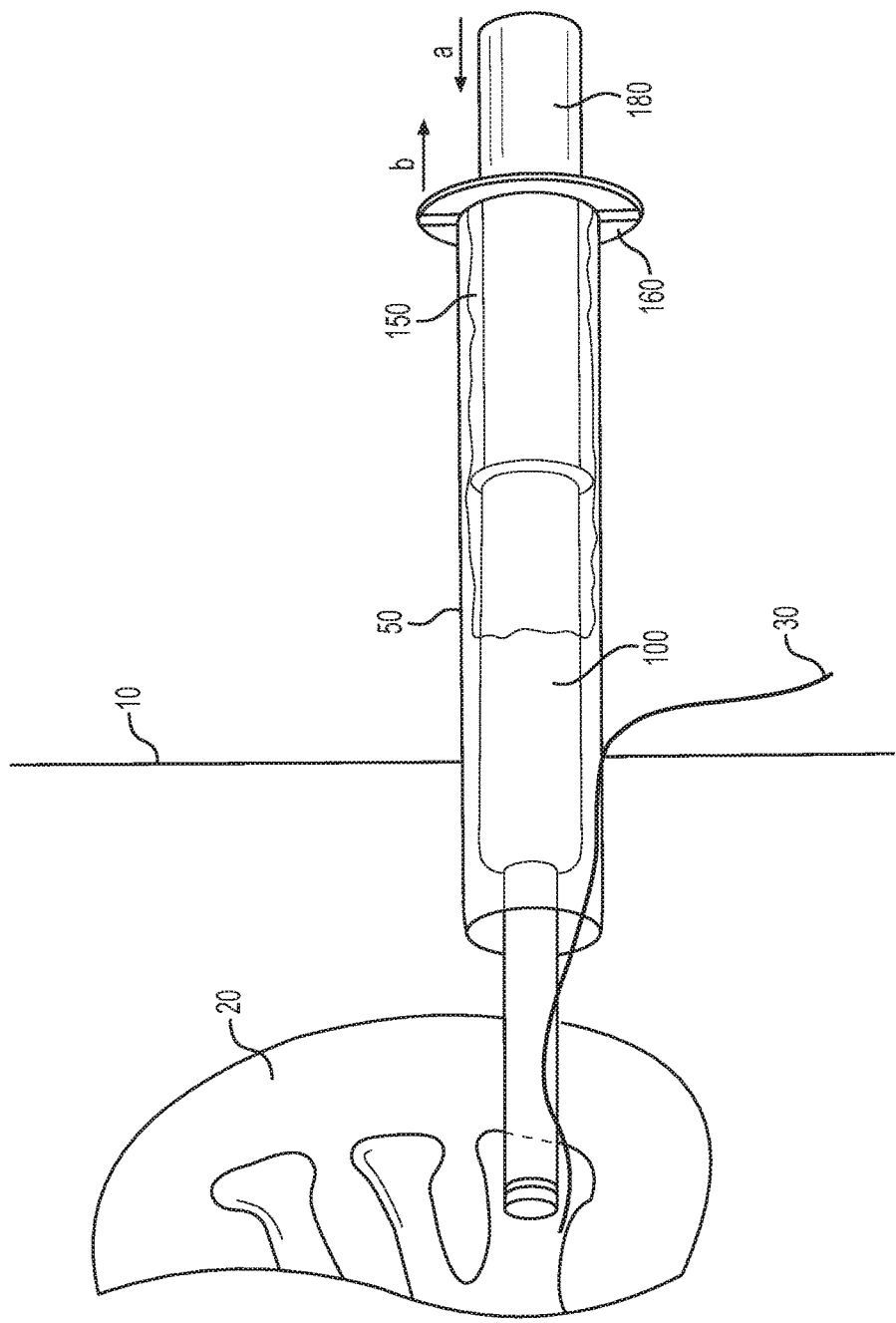
FIG. 5 is a side view of an embodiment of a hemostatic device in use.
Figure 6B:
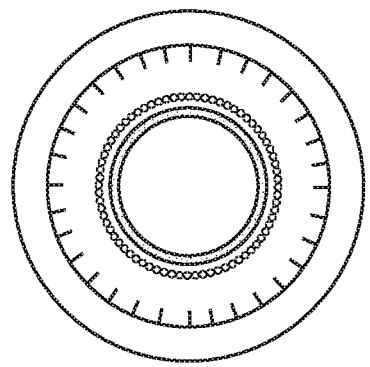
FIG. 6B is a cross-sectional view of the hemostatic device shown in FIG. 6A.
Figure 6A:
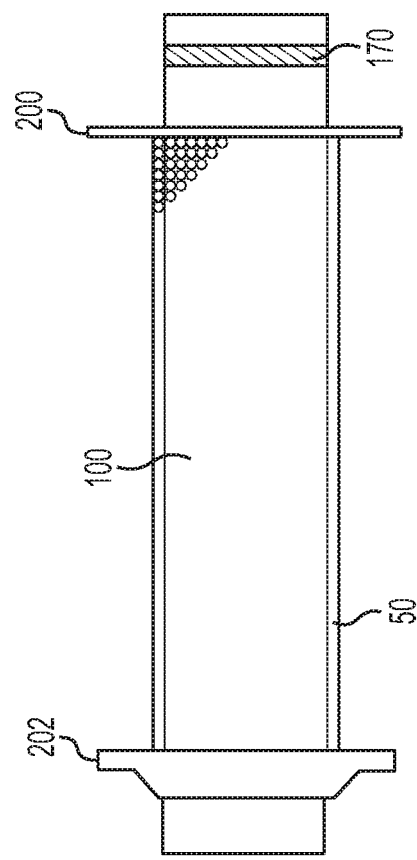
FIG. 6A is a side view of an exemplary embodiment of a hemostatic device.
Figure 6C:
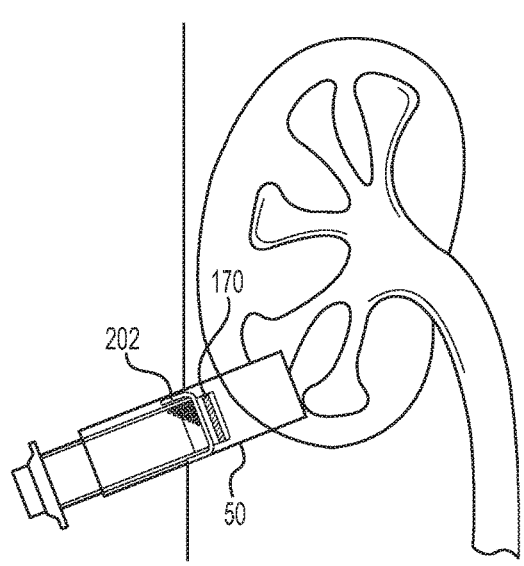
FIGS. 6C-6E are side views of exemplary embodiments of a hemostatic device in use.
Figure 6D:
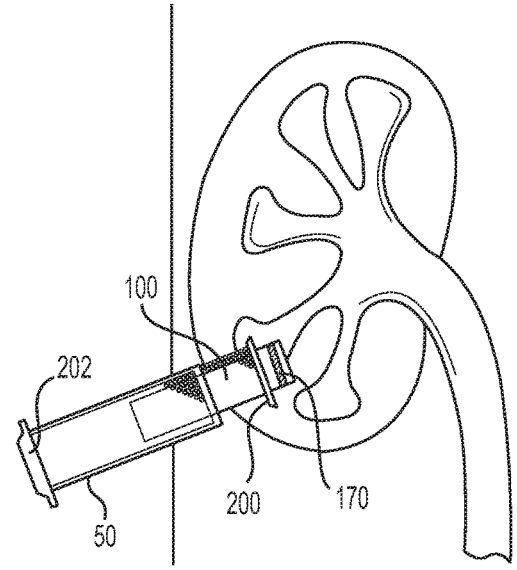
Figure 6E:
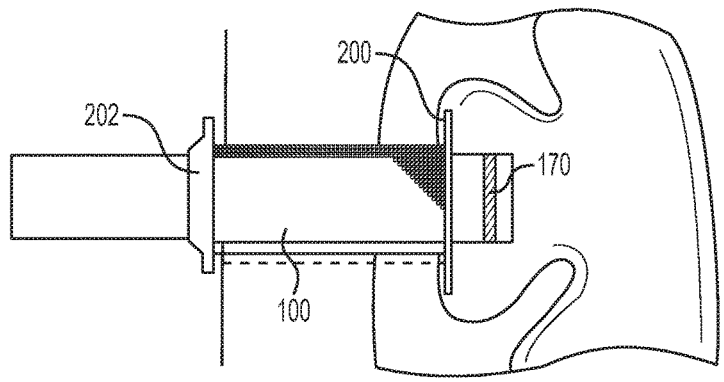

FIGS. 4 and 5 depict embodiments of methods for using device 100. Once a medical procedure (e.g., a kidney stone removal or a kidney biopsy) is complete and other medical devices are removed from percutaneous sheath 50, device 100 can be inserted into sheath 50 until distal end 125 reaches kidney 20 (e.g., the distal end of sheath 50 within kidney 20). A user then can insert a driver (e.g., cylindrical driver 180 having distal end 185) into percutaneous sheath 50 (as indicated by the arrow in FIG. 4), advancing driver 180 until distal end 185 contacts proximal end 115 of cylinder 105. In some embodiments, cylinder 105 can have a shelf or protrusion at or adjacent to proximal end 115, on which driver 180 can seat and be used to exert force on cylinder 105 in a distal direction. The user then can remove percutaneous sheath 50 from the subject by pulling it over driver 180. Simultaneously or subsequently, the user can move handle 160 in a proximal direction, pulling barrier 150 over exterior surface 130 of cylinder 105 and removing barrier 150 from the subject's body while holding cylinder 105 in place. This can be accomplished, for example, by exerting force in a distal direction on driver 180 (arrow "a" in FIG. 5) while exerting force in a proximal direction on handle 160 (arrow "b" in FIG. 5). In some embodiments, the action of removing sheath 50 can also move handle 160 in a proximal direction. In either embodiment, such movement can expose hemostatic material 140 to the subjects kidney and any other tissue surrounding device 100 within the subject's body. It is noted that driver 180 can be hollow such that a lumen extends through its length. Such a hollow driver, in combination with a hollow hemostatic device can allow a user to insert or maintain wires or other instruments into the subject's kidney as needed.

In some embodiments, the device 100 may have a retention disk 200 located near the distal end 125. As shown in FIGS. 6-12, retention disk 200 anchors the device 100 in the kidney, seal the hemostatic material inside the percutaneous tract, and isolate or separate the hemostatic process occurring along the shaft from the surgical intervention occurring through the lumen of the device. The retention disk 200 also assists in hemostasis by providing pressure. The device 100 may have a collar 202 that can be positioned against the outside surface of the target organ which will aiding in securing the device in location. When positioned against the outside surface of the target organ, such as a kidney, the collar 202 creates a barrier at the end of the device to temporarily seal the hemostatic material in the percutaneous tract located between the collar 202 and the retention disk 200.

Figure 7A:
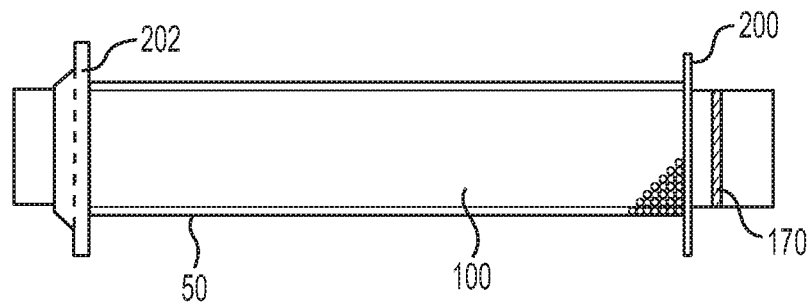
FIGS. 7A-7B are side views of exemplary embodiments of a hemostatic device.
Figure 7B:
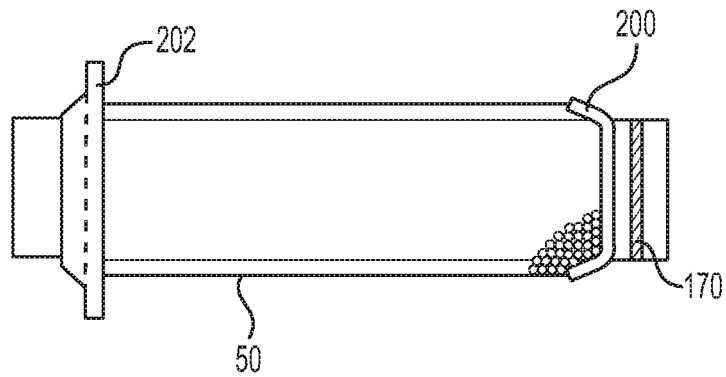
Figure 7C:
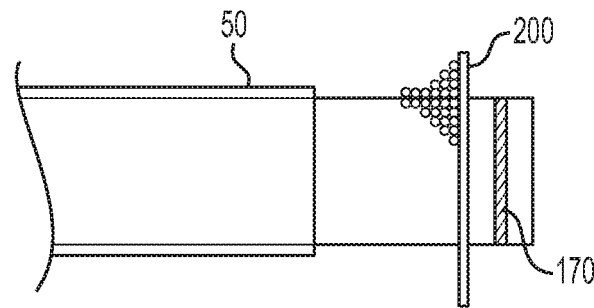
FIGS. 7C-7G are partial side views of exemplary embodiments of a hemostatic device.
Figure 7D:
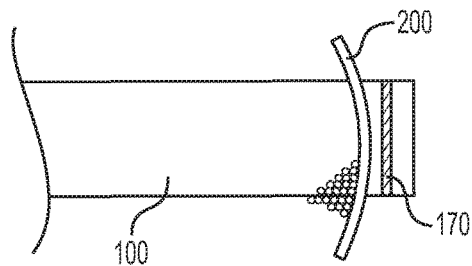
Figure 7E:
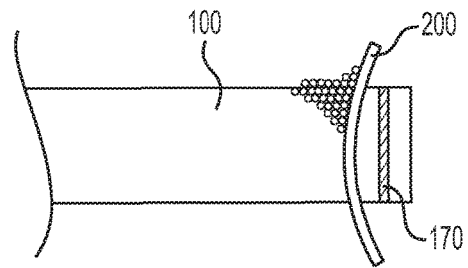
Figure 7F:
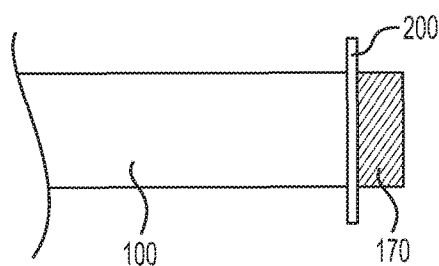
Figure 7G:
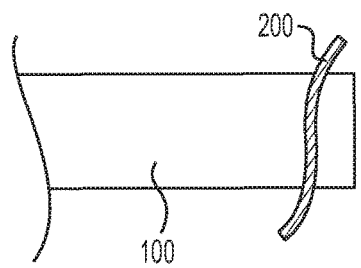
Figure 9C:
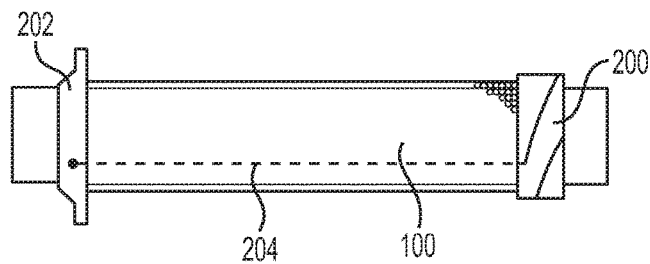
FIG. 9C is a side view of an exemplary embodiment of a hemostatic device in use.
Figure 9C:
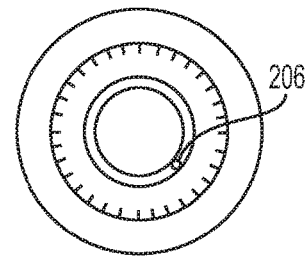
Figure 9C:
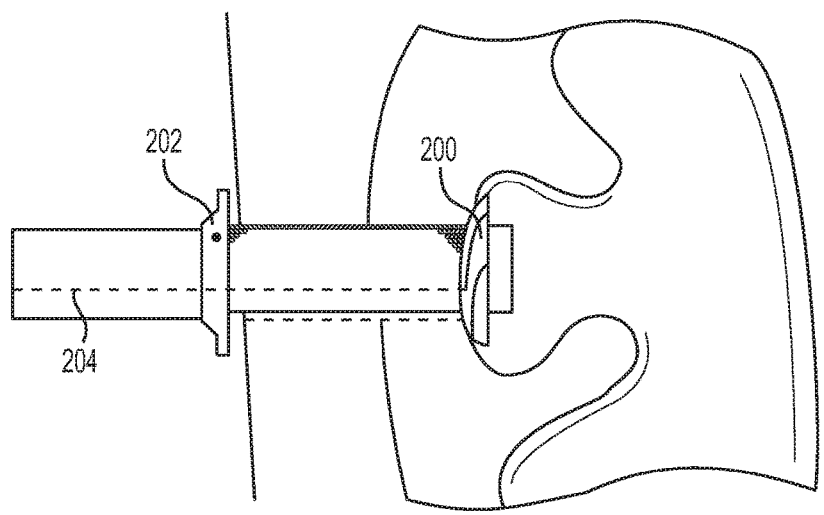

As shown in FIGS. 6A-E, 7A-G, and 8A-I, the retention disk 200 may be constructed of flexible plastic or other suitable flexible material. The retention disk may be flexible such that when the device 100 is inside the percutaneous sheath 50, the retention disk 200 is bent backward or collapsed by the inner walls of the percutaneous sheath 50, as shown for example in FIGS. 6C and 7B. After the device 100 and sheath 50 are inserted into the percutaneous tract, the sheath 50 is removed, thereby allowing the retention disk 200 to deploy into position, as shown for example in FIGS. 6D and 6E. The collar 202 of the device 100 may be slidably attached to the device 100. After the sheath 50 is removed, the collar 202 may be slid into position against the outside surface of the kidney, as shown for example in FIG. 6E. Positioning the collar 202 against the outside surface of the target organ provides compression between the collar 202 and the retention disk 200, and also traps hemostatic material inside the percutaneous tract. The retention disk 200 may be constructed such that it assumes a concave shape after deployment, as shown in FIG. 7D. The retention disk 200 may be constructed such that it assumes a convex shape after deployment, as shown in FIG. 7E. The retention disk 200 may be constructed such it may be a variation of concave and convex depending on orientation and deployment, as shown in FIG. 7G.

One or more radio-opaque markers 170 may be located near the retention disk 200 so that the position of device 100 and retention disk 200 can be observed radiographically during deployment. The radio-opaque markers 170 could be located between the retention disk 200 and the distal end 125. The radio-opaque markers 170 could be located on all or a portion of the device 100 located between the retention disk 200 and the distal end 125. In addition, or alternatively, the radio-opaque markers 170 could be located inside the retention disk 200.

Figure 10G:
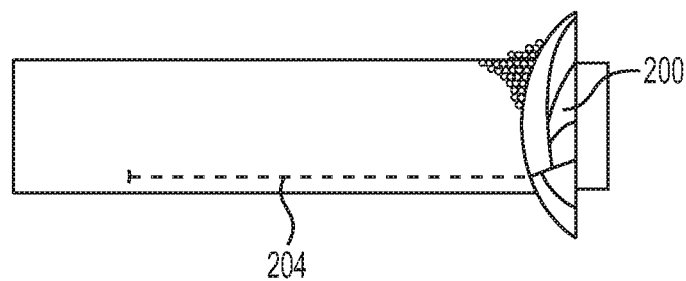
Figure 10H:
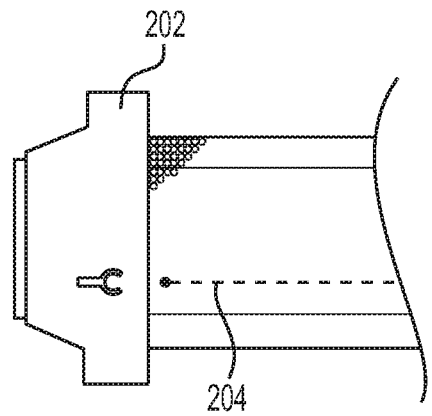
Figure 10I:
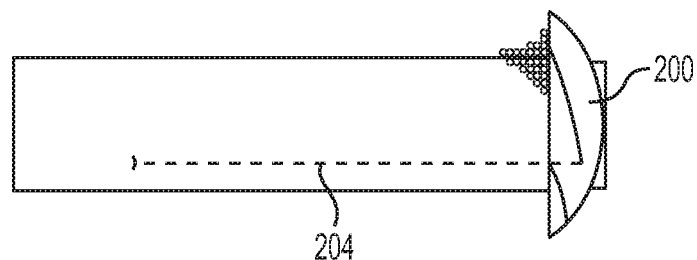
Figure 11B:
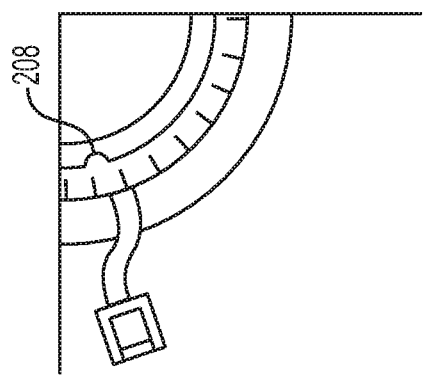
FIG. 11B is a partial cross-sectional view of the hemostatic device shown in FIG. 11A.
Figure 11A:
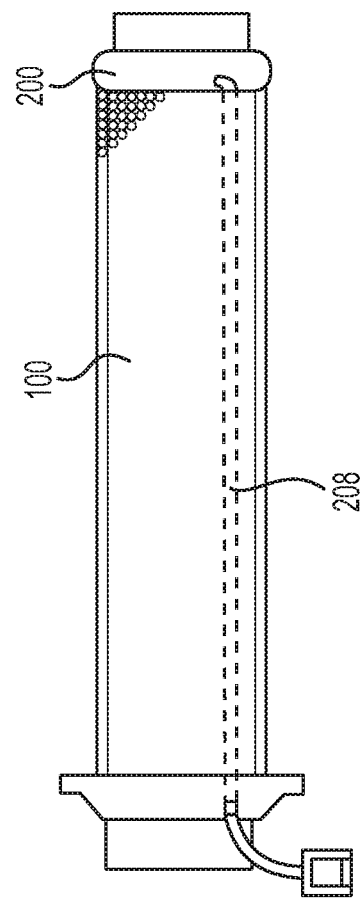
FIG. 11A is side view of an exemplary embodiment of a hemostatic device.
Figure 11C:
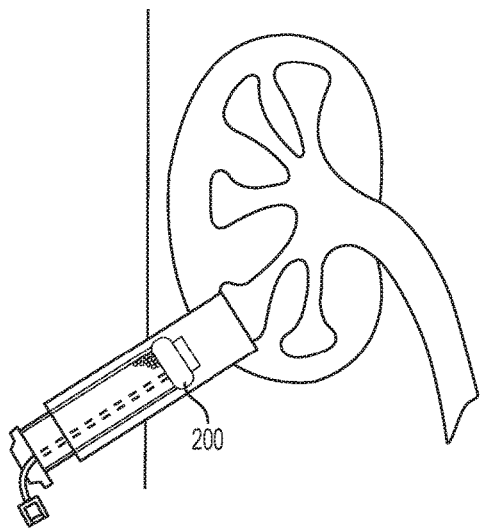
FIGS. 11C-11D are side views of an exemplary embodiment of a hemostatic device in use.
Figure 11D:
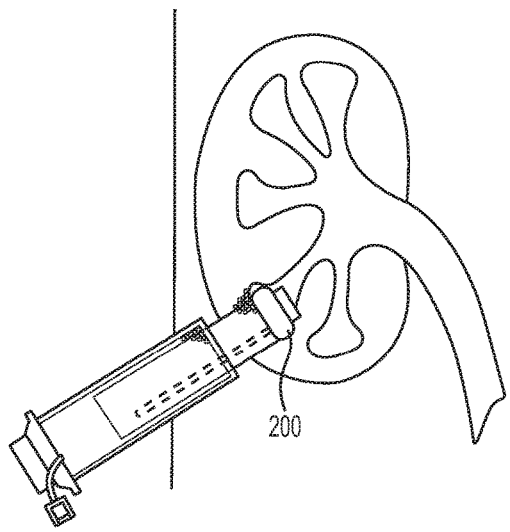
Figure 11E:
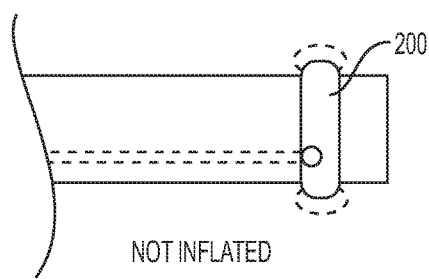
FIGS. 11E-11F are partial side views of a portion of the hemostatic device shown in FIGS. 11C-11D.
Figure 11F:
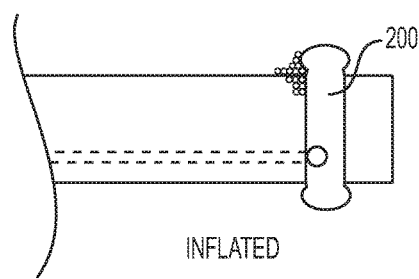

As shown in FIGS. 9A-C and 10A-I, deployment of the retention device 200 may be driven or controlled by control element 204. Control element 204 may be a wire, string or other suitable device, depending on deployment of the retention disk 200. The control element 204 may be positioned inside and along the length of the wall of the device 100. One end of the control element 204 may be attached to the collar 202. The other end of the control element 204 may be positioned inside the retention disk 200 and may extend around the circumference of the retention disk 100. The device 100 may have one or more channels 206 inside the wall of the device 100 for containing the control element 204 located between collar 202 and the retention disk 200. The retention disk 202 may be deployed by pushing the control elements 204 toward the distal end 125 or by pulling the control elements 204 away from distal end 125. For example, the device 100 and retention disk 200 may be constructed such that when the control elements 204 are pushed toward the distal end 125, the flexible material of the retention disk 200 changes from a collapsed configuration to an expanded configuration in an umbrella-like fashion. Alternatively, when the control element 204 is attached to the collar 202, the flexible plastic or other suitable material of the retention disk 200 may be in a collapsed configuration. When the control element 204 is released from the collar 204, the flexible plastic or other suitable material of the retention disk 200 is allowed to expand into its deployment shape. The retention disk 200 may be constructed such that it assumes a concave shape after deployment, as shown in FIGS. 10A-E. The retention disk 200 may be constructed such that it assumes a convex shape after deployment, as shown in FIG. 10I. After the device 100 is inserted into the kidney, the retention disk is deployed, and the sheath 50 is removed, the collar 202 may be slid into position against the outside surface of the kidney.

As shown in FIGS. 11A-F, the retention disk 200 may be constructed of inflatable material. Prior to the device 100 being inserted into the kidney, the retention disk 200 is in the uninflated state. After the device 100 is inserted into the kidney, the retention disk 200 can be deployed by inflating the inflatable material of the retention disk 200. The device 100 may have one or more channels 208 inside the wall of the device 100 for using inflating the retention disk 200. The retention disk 200 may be inflated with air or liquid. In one of the embodiments, the retention disk 200 may be inflated with radio-opaque contrast material to allow radiographic imaging for observing the placement of the device 100 and retention disk 200 in the organ. After the device 100 is inserted into the kidney, the retention disk 200 is inflated, and the sheath 50 is removed, the collar 202 may be slid into position against the outside surface of the kidney.

Figure 12B:
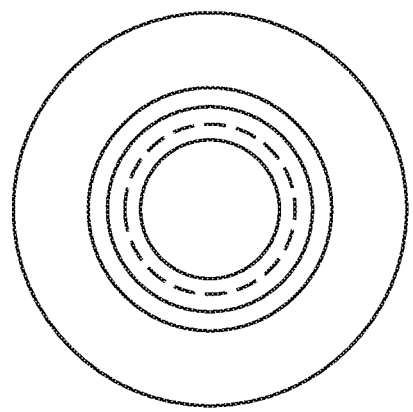
FIG. 12B is a cross-sectional view of the hemostatic device shown in FIG. 12A.
Figure 12A:
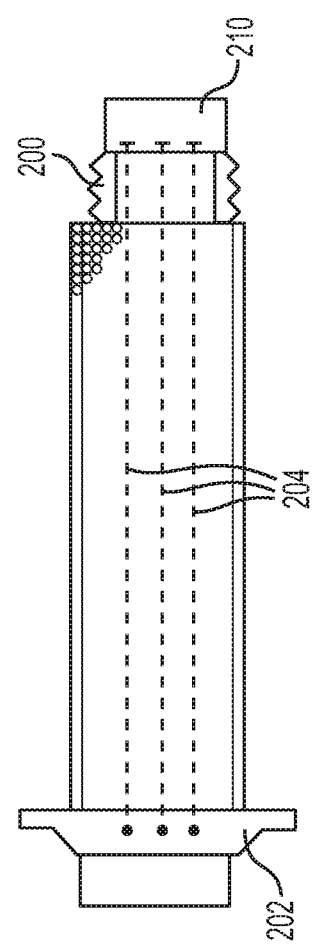
FIG. 12A is a side view of an exemplary embodiment of a hemostatic device.
Figure 12C:
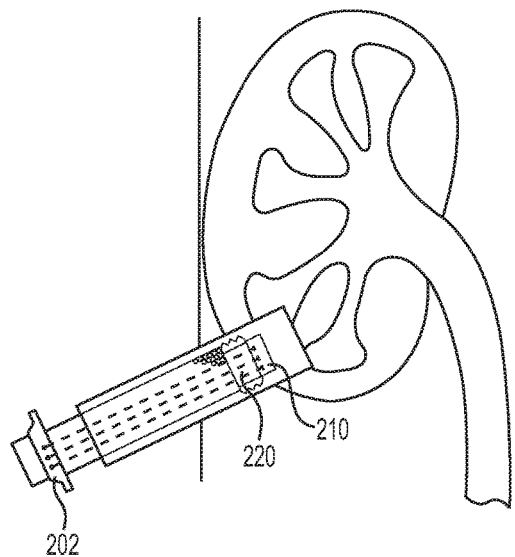
FIGS. 12C-12D are side views of exemplary embodiments of a hemostatic device in use.
Figure 12D:
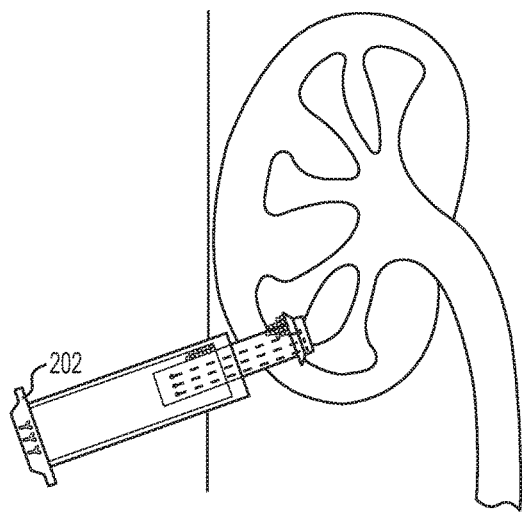
Figure 12E:
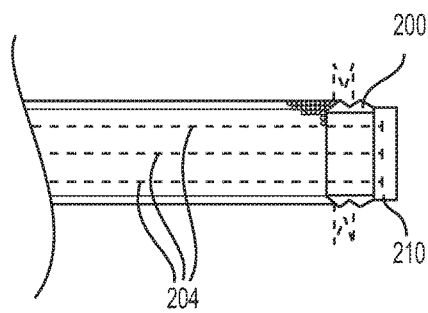
FIGS. 12E-12F are partial side views of exemplary embodiments of a hemostatic device.
Figure 12F:
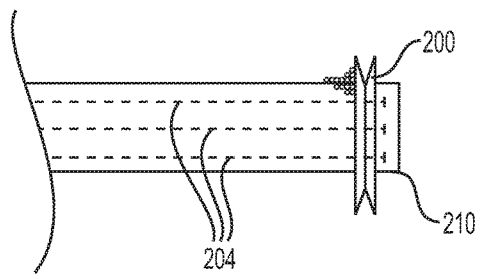

As shown in FIGS. 12A-F, the retention disk 200 may comprise collapsible material, such as flexible plastic or other suitable material, located between the main body of the device 100 and a distal member 210 of the device 100. The material of the retention disk 200 may be a less stiff material that the material comprising the main body of the device 100 and the distal member 210. Ends of control elements 204 may be secured to the collar 202. The other ends of the control elements 204 may be secured to distal member 210. The device 100 may have one or more channels 212 inside the wall of the main body of the device 100 for containing the control element 204. Sliding the collar 202 away from the distal end 125 pulls the control elements 204 causing the distal member 210 to be pulled toward the proximal end 115. This, in turn, causes the flexible material of the retention disk 200 to tent up to form a deployment shape, as shown in FIGS. 12E-F.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A hemostatic device for use in an internal organ comprising:
   an elongate member configured for insertion into a kidney, the elongate member having an exterior surface, a distal end and a proximal end, and a first lumen defined by an interior surface of the elongate member extending from the distal end to the proximal end, the first lumen configured to permit surgical implements to pass through the elongate member after the elongate member is inserted in a percutaneous tract of the kidney; a hemostatic material located on the exterior surface;
   a removable covering adapted to move slidably over the elongate member and the hemostatic material;
   a plurality of channels on the exterior surface and configured to retain the hemostatic material on the exterior surface;
   wherein the elongate member configured to achieve hemostasis after the surgical implements are removed from the first lumen by the simultaneous application of the hemostatic material and pressure exerted by the exterior surface of the elongate member while surgery is performed on the internal organ using the surgical implements placed in and through the first lumen from the distal end to the proximal end; and wherein the elongate member comprises a retention disk located near the distal end for securing the elongate member to an interior wall of the percutaneous tract;
   a collar slidably connected to the elongate member and configured to be slid into a position against an exterior wall of the percutaneous tract for securing the elongate member to the exterior wall of the percutaneous tract after deployment of the retention disk;
   a control element located inside a second lumen in the elongate member and configured to control deployment of the retention disk, wherein a first end of the control element is attached to the retention disk and a second end of the control element is attached to the collar, wherein the retention disk is configured to change from a collapsed configuration to a deployed configuration, and the control element is configured to move the retention disk toward the proximal end of the elongate member for operable engagement with the interior wall of the percutaneous tract.

2. The hemostatic device of claim 1, wherein the retention disk is inflatable.

3. The hemostatic device of claim 1, wherein the retention disk is inflated with radio-opaque contrast material to allow radiographic of the retention disk in the kidney.

* * * * *